US008853372B2

(12) United States Patent
Beck et al.

(10) Patent No.: US 8,853,372 B2
(45) Date of Patent: *Oct. 7, 2014

(54) SACCHARIDE SILOXANES STABLE IN AQUEOUS ENVIRONMENTS AND METHODS FOR THE PREPARATION AND USE OF SUCH SACCHARIDE SILOXANES

(75) Inventors: James Anderson Beck, Midland, MI (US); Lylenette Canfield, Midland, MI (US); Michael Salvatore Ferritto, Midland, MI (US); Eric Jude Joffre, Midland, MI (US); Mark Keinath, Saginaw, MI (US); Feifei Lin, Midland, MI (US); Anil Kumar Tomar, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/810,916

(22) PCT Filed: Aug. 2, 2011

(86) PCT No.: PCT/US2011/046190
§ 371 (c)(1),
(2), (4) Date: Jan. 18, 2013

(87) PCT Pub. No.: WO2012/027073
PCT Pub. Date: Mar. 1, 2012

(65) Prior Publication Data
US 2013/0115184 A1 May 9, 2013

Related U.S. Application Data

(60) Provisional application No. 61/375,938, filed on Aug. 23, 2010.

(51) Int. Cl.
| | | |
|---|---|---|
| C07H 1/00 | (2006.01) | |
| C07H 15/00 | (2006.01) | |
| C08B 37/00 | (2006.01) | |
| A61K 31/70 | (2006.01) | |
| A61Q 5/12 | (2006.01) | |
| C08G 77/42 | (2006.01) | |
| A61K 8/58 | (2006.01) | |
| A61Q 19/00 | (2006.01) | |
| C08G 77/388 | (2006.01) | |
| A61K 8/898 | (2006.01) | |
| C07F 7/18 | (2006.01) | |
| A61Q 15/00 | (2006.01) | |
| A61Q 1/02 | (2006.01) | |
| A61Q 5/02 | (2006.01) | |
| A61Q 5/06 | (2006.01) | |

(52) U.S. Cl.
CPC .............. *C07F 7/1804* (2013.01); *C08G 77/42* (2013.01); *A61K 2800/10* (2013.01); *A61Q 15/00* (2013.01); *A61Q 1/02* (2013.01); *A61Q 5/02* (2013.01); *A61K 8/585* (2013.01); *A61Q 19/00* (2013.01); *A61Q 5/12* (2013.01); *C08G 77/388* (2013.01); *A61K 8/898* (2013.01); *A61Q 5/06* (2013.01)

USPC .............. 536/1.11; 536/4.1; 536/124; 514/23; 514/25; 514/63; 424/70.12

(58) Field of Classification Search
USPC ................ 536/1.11, 4.1, 124; 514/23, 25, 63; 424/70.12
See application file for complete search history.

(56) References Cited

U.S. PATENT DOCUMENTS

| | | | |
|---|---|---|---|
| 2,676,182 | A | 4/1954 | Daudt et al. |
| 2,857,356 | A | 10/1958 | Goodwin |
| 3,159,601 | A | 12/1964 | Ashby |
| 3,220,972 | A | 11/1965 | Lamoreaux |
| 3,296,291 | A | 1/1967 | Chalk |
| 3,419,593 | A | 12/1968 | Willing |
| 3,445,420 | A | 5/1969 | Kookootsedes et. al. |
| 3,516,946 | A | 6/1970 | Modic et. al. |
| 3,814,730 | A | 6/1974 | Karstedt |
| 3,936,582 | A | 2/1976 | Keiser |
| 3,989,667 | A | 11/1976 | Lee et al. |
| 3,989,668 | A | 11/1976 | Lee et al. |
| 4,263,274 | A | 4/1981 | Kulkarni |
| 4,269,603 | A | 5/1981 | Worth |
| 4,310,469 | A | 1/1982 | Crivello |
| 4,313,988 | A | 2/1982 | Koshar et al. |
| 4,370,358 | A | 1/1983 | Hayes et al. |
| 4,447,562 | A | 5/1984 | Ivani |
| 4,501,861 | A | 2/1985 | Woodbrey |
| 4,558,110 | A | 12/1985 | Lee |

(Continued)

FOREIGN PATENT DOCUMENTS

| | | |
|---|---|---|
| CA | 711756 | 6/1965 |
| DE | 19918627 | 10/2000 |

(Continued)

OTHER PUBLICATIONS

Akimoto, T. et al. "Preparation of Oligodimethylsiloxanes with Sugar Moiety at a Terminal Group as a Transdermal Penetration Enhancer." Macromolecular Chemistry and Physics. vol. 201, No. 18, Dec. 2000, pp. 2729-2734 (6 pages).

(Continued)

*Primary Examiner* — Shaojia Anna Jiang
*Assistant Examiner* — Michael C Henry

(57) ABSTRACT

A novel saccharide siloxane copolymer has improved stability in the presence of water as compared to certain previously known saccharide siloxanes. The saccharide siloxane copolymer is useful in personal care compositions.

18 Claims, No Drawings

(56) References Cited

U.S. PATENT DOCUMENTS

| | | |
|---|---|---|
| 4,584,355 A | 4/1986 | Blizzard |
| 4,584,361 A | 4/1986 | Janik |
| 4,585,836 A | 4/1986 | Homan |
| 4,591,622 A | 5/1986 | Blizzard |
| 4,591,652 A | 5/1986 | Dasquale et al. |
| 4,604,442 A | 8/1986 | Rich |
| 4,631,329 A | 12/1986 | Gornowicz |
| 4,707,531 A | 11/1987 | Shirahata |
| 4,760,025 A | 7/1988 | Estell et al. |
| 4,766,176 A | 8/1988 | Lee |
| 4,774,281 A | 9/1988 | Chaffee et al. |
| 4,784,879 A | 11/1988 | Lee et al. |
| 4,793,555 A | 12/1988 | Lee et al. |
| RE33,141 E | 1/1990 | Gornowicz et al. |
| 4,939,128 A | 7/1990 | Kato et al. |
| 4,962,076 A | 10/1990 | Chu et al. |
| 4,999,437 A | 3/1991 | Dobler et al. |
| 5,004,791 A | 4/1991 | Billmers |
| 5,011,870 A | 4/1991 | Peterson |
| 5,015,700 A | 5/1991 | Herzig et al. |
| 5,017,654 A | 5/1991 | Togashi et al. |
| 5,036,117 A | 7/1991 | Chung et al. |
| 5,051,455 A | 9/1991 | Chu et al. |
| 5,053,442 A | 10/1991 | Chu et al. |
| 5,075,038 A | 12/1991 | Cole et al. |
| 5,087,443 A | 2/1992 | Chizat et al. |
| 5,175,325 A | 12/1992 | Brown et al. |
| 5,227,093 A | 7/1993 | Cole et al. |
| 5,252,233 A | 10/1993 | Czech |
| RE34,606 E | 5/1994 | Estell et al. |
| 5,310,843 A | 5/1994 | Morita |
| 5,352,724 A | 10/1994 | Fujiki et al. |
| 5,380,527 A | 1/1995 | Legrow et al. |
| 5,493,041 A | 2/1996 | Biggs et al. |
| 5,626,660 A | 5/1997 | Lautenschlager et al. |
| 5,654,362 A | 8/1997 | Schulz, Jr. et al. |
| 5,665,155 A | 9/1997 | Hohner et al. |
| 5,677,163 A | 10/1997 | Mainzer et al. |
| 5,700,676 A | 12/1997 | Bott et al. |
| 5,747,016 A | 5/1998 | Yui et al. |
| 5,831,080 A | 11/1998 | Sejpka et al. |
| 5,891,977 A | 4/1999 | Dietz et al. |
| 5,895,794 A | 4/1999 | Berg et al. |
| 5,972,682 A | 10/1999 | Bott et al. |
| 5,981,680 A | 11/1999 | Petroff et al. |
| 5,990,069 A | 11/1999 | Andre et al. |
| 6,043,328 A | 3/2000 | Domschke et al. |
| 6,051,216 A | 4/2000 | Barr et al. |
| 6,066,326 A | 5/2000 | Afriat et al. |
| 6,066,727 A | 5/2000 | Yamamoto et al. |
| 6,132,822 A | 10/2000 | Overcash et al. |
| 6,136,758 A | 10/2000 | Yamada et al. |
| 6,218,560 B1 | 4/2001 | Abele et al. |
| 6,221,979 B1 | 4/2001 | Lin et al. |
| 6,239,194 B1 | 5/2001 | Standke et al. |
| 6,255,429 B1 | 7/2001 | Griffin et al. |
| 6,361,716 B1 | 3/2002 | Kleyer et al. |
| 6,372,833 B1 | 4/2002 | Chen et al. |
| 6,391,322 B1 | 5/2002 | Roulier et al. |
| 6,398,911 B1 | 6/2002 | Schroeder et al. |
| 6,414,139 B1 | 7/2002 | Unger et al. |
| 6,433,055 B1 | 8/2002 | Kleyer et al. |
| 6,436,382 B1 | 8/2002 | Chopra et al. |
| 6,440,429 B1 | 8/2002 | Torizuka et al. |
| 6,448,329 B1 | 9/2002 | Hirschi et al. |
| 6,465,550 B1 | 10/2002 | Kleyer et al. |
| 6,471,952 B1 | 10/2002 | Dubief et al. |
| 6,471,985 B2 | 10/2002 | Guyuron et al. |
| 6,485,716 B1 | 11/2002 | Fei et al. |
| 6,500,883 B1 | 12/2002 | Mack et al. |
| 6,506,444 B1 | 1/2003 | Mahr et al. |
| 6,517,933 B1 | 2/2003 | Soane et al. |
| 6,521,084 B1 | 2/2003 | Burger et al. |
| 6,534,581 B1 | 3/2003 | Kleyer et al. |
| 6,762,289 B1 | 7/2004 | O'Lenick, Jr. et al. |
| 6,783,692 B2 | 8/2004 | Bhagwagar |
| 6,791,839 B2 | 9/2004 | Bhagwagar |
| 6,815,486 B2 | 11/2004 | Bhagwagar et al. |
| 7,005,281 B2 | 2/2006 | Ohrlein et al. |
| 7,074,490 B2 | 7/2006 | Feng et al. |
| 7,199,205 B2 | 4/2007 | Okawa et al. |
| 7,205,373 B2 | 4/2007 | Brandstadt et al. |
| 7,208,561 B2 | 4/2007 | Yoshitake et al. |
| 7,354,982 B2 | 4/2008 | Yoshitake et al. |
| 7,649,087 B2 | 1/2010 | Yoshitake et al. |
| 7,741,253 B2 | 6/2010 | Hanes |
| 7,834,087 B2 | 11/2010 | Joffre et al. |
| 7,871,987 B2 | 1/2011 | McSuliffe et al. |
| 2001/0021387 A1 | 9/2001 | Krammer et al. |
| 2001/0053897 A1 | 12/2001 | Frate et al. |
| 2003/0202948 A1 | 10/2003 | Koini et al. |
| 2004/0071746 A1 | 4/2004 | Popplewell et al. |
| 2004/0077816 A1 | 4/2004 | Brandstadt et al. |
| 2004/0082024 A1 | 4/2004 | Brandstadt et al. |
| 2004/0091541 A1 | 5/2004 | Unger |
| 2004/0091730 A1 | 5/2004 | Hart et al. |
| 2004/0241130 A1 | 12/2004 | Tamareselvy et al. |
| 2004/0247552 A1 | 12/2004 | Blin et al. |
| 2004/0254275 A1 | 12/2004 | Fukui et al. |
| 2005/0043365 A1 | 2/2005 | Yoshitake et al. |
| 2006/0013791 A1 | 1/2006 | Shimizu et al. |
| 2006/0216259 A1 | 9/2006 | Haubennestel |
| 2008/0138386 A1 | 6/2008 | Joffre et al. |
| 2008/0199417 A1 | 8/2008 | Joffre et al. |
| 2008/0200612 A1 | 8/2008 | Joffre et al. |
| 2008/0209645 A1 | 9/2008 | Carrillo et al. |
| 2009/0169501 A1 | 7/2009 | Feng et al. |
| 2009/0258058 A1 | 10/2009 | Thomas et al. |
| 2010/0105582 A1 | 4/2010 | Joffre et al. |

FOREIGN PATENT DOCUMENTS

| | | |
|---|---|---|
| EP | 0180377 | 5/1986 |
| EP | 0300525 | 1/1989 |
| EP | 0363252 | 4/1990 |
| EP | 0438496 | 7/1991 |
| EP | 0444921 | 9/1991 |
| EP | 0465744 | 1/1992 |
| EP | 0506241 | 9/1992 |
| EP | 0572416 | 9/1992 |
| EP | 0347895 | 11/1993 |
| EP | 0698633 | 2/1996 |
| EP | 0562922 | 5/1997 |
| EP | 0848029 | 6/1998 |
| EP | 0865787 | 9/1998 |
| EP | 0869142 | 10/1998 |
| EP | 0874017 | 10/1998 |
| EP | 0934959 | 8/1999 |
| EP | 0962482 | 12/1999 |
| EP | 1020494 | 2/2000 |
| EP | 1057872 | 12/2000 |
| EP | 1201817 | 5/2002 |
| EP | 1331248 | 7/2007 |
| GB | 2407496 | 5/2005 |
| JP | 62-068820 | 4/1987 |
| JP | 63-139106 | 6/1988 |
| JP | 03-290127 | 12/1991 |
| JP | 61-096593 | 12/1992 |
| JP | 5-186596 | 7/1993 |
| JP | 5-331291 | 12/1993 |
| JP | 7-041414 | 2/1995 |
| JP | 7-041415 | 2/1995 |
| JP | 7-041416 | 2/1995 |
| JP | 7-041417 | 2/1995 |
| JP | 7-070204 | 3/1995 |
| JP | 07-133352 | 5/1995 |
| JP | 8-134103 | 5/1996 |
| JP | 8-269204 | 10/1996 |
| JP | 9-136901 | 5/1997 |
| JP | 09-202714 | 8/1997 |
| JP | 10-029910 | 2/1998 |
| JP | 10-029915 | 2/1998 |
| JP | 10-029921 | 2/1998 |
| JP | 10-053797 | 2/1998 |

(56) References Cited

FOREIGN PATENT DOCUMENTS

| | | |
|---|---|---|
| JP | 10-298288 | 11/1998 |
| JP | 11-092490 | 4/1999 |
| JP | 11-106310 | 4/1999 |
| JP | 10-512000 | 11/1999 |
| JP | 11-343347 | 12/1999 |
| JP | 11-349450 | 12/1999 |
| JP | 11-349601 | 12/1999 |
| JP | 2002-146025 | 5/2002 |
| JP | 2006-290837 | 10/2006 |
| JP | 2009-057380 | 3/2009 |
| WO | 90/03809 | 4/1990 |
| WO | 92/14428 | 9/1992 |
| WO | 94/29322 | 12/1994 |
| WO | 94/29324 | 12/1994 |
| WO | 96/15309 | 5/1996 |
| WO | 96/18729 | 6/1996 |
| WO | 98/49998 | 11/1998 |
| WO | 98/50006 | 11/1998 |
| WO | 99/55953 | 11/1999 |
| WO | 00/78844 | 12/2000 |
| WO | 01/25385 | 4/2001 |
| WO | 01/96450 | 12/2001 |
| WO | 02/41709 | 5/2002 |
| WO | 02/088456 | 11/2002 |
| WO | 03/020770 | 3/2003 |
| WO | 03/042283 | 5/2003 |
| WO | 03/050144 | 6/2003 |
| WO | 2004/016626 | 2/2004 |
| WO | 2004/108175 | 12/2004 |
| WO | 2005/047378 | 5/2005 |
| WO | 2005/063855 | 7/2005 |
| WO | 2006/025552 | 3/2006 |
| WO | 2006/064928 | 6/2006 |
| WO | 2006/065282 | 6/2006 |
| WO | 2006/066227 | 6/2006 |
| WO | 2006/071772 | 7/2006 |
| WO | 2006/107003 | 10/2006 |
| WO | 2006/107004 | 10/2006 |
| WO | 2006/127883 | 11/2006 |
| WO | 2006127924 | 11/2006 |
| WO | 2007/139812 | 12/2007 |
| WO | 2008/046763 | 4/2008 |
| WO | 2008/103219 | 8/2008 |
| WO | 2009/019144 | 2/2009 |
| WO | 2009/052272 | 4/2009 |
| WO | 2009/079610 | 6/2009 |
| WO | 2009/125126 | 10/2009 |
| WO | 2009/150846 | 12/2009 |

OTHER PUBLICATIONS

Database WPI Derwent Publications Ltd., London, GB; AN 1988-201757.
Gupta, R. et al. "Lipase Assays for Conventional and Molecular Screening: An Overview." Biotechnology and Applied Biochemistry. vol. 37, No. 1, Feb. 2003, pp. 63-71 (9 pages).
Hardman, B. et al. "Silicones" in: *Encyclopedia of Polymer Science and Engineering*; vol. 15: Scattering to Structural Foams; John Wiley & Sons, Inc. (New York 1989) p. 243 (3 pages).
Lindhorst, T.K. "Protecting Groups for Carbohydrates." in: Lindhorst, T.K., *Essentials of Carbohydrate Chemistry and Biochemistry*; Wiley-VCH Verlag GmbH & Co. (Weinheim 2003), Second Revised and Updated Edition, pp. 39-78 (23 pages).
Muraoka, T. et al. "Hair preparations containing organopolysiloxanes having sugar substituents," XP002402424, Database accession No. 1989: 179250; Chemical Abstracts Service, Columbus, Ohio, US; May 12, 1989.
Pearson, A.J. et al. "Handbook of Reagents for Organic Synthesis: Activating Agents and Protecting Groups." John Wiley & Sons (Chichester 1999), pp. 102, 205, 416, 417 (6 pages).
Simionescu, Bogdan C., Valeria Harabagiu and Cristofor I. Simionescu, "Siloxane-Containing Polymers" in The Polymeric Materials Encyclopedia, CRC Press, Inc., 1996.
Wagner, R. et al. "Silicon-Modified Carbohydrates Surfactants III: Cationic and Anionic Compounds." Applied Organometallic Chemistry, vol. 11, No. 6, Jun. 1997, pp. 523-538 (16 pages).
International Search Report and Written Opinion mailed Sep. 28, 2011 which issued in corresponding International Patent Application No. PCT/US2011/046190 (8 pages).

SACCHARIDE SILOXANES STABLE IN AQUEOUS ENVIRONMENTS AND METHODS FOR THE PREPARATION AND USE OF SUCH SACCHARIDE SILOXANES

CROSS REFERENCE TO RELATED APPLICATIONS

This application is a U.S. national stage filing under 35 U.S.C. §371 of PCT application Ser. No. PCT/U.S.11/46190 filed on Aug. 20, 2011, currently pending, which claims the benefit of U.S. Provisional Patent Application No. 61/375938 filed Aug. 23, 2010 under 35 U.S.C. §119 (e). PCT Application No. PCT/U.S.11/46190 and U.S. Provisional Patent Application No. 61/375938 are hereby incorporated by reference.

BACKGROUND OF THE INVENTION

Saccharide siloxanes are known in the art. Saccharide siloxanes comprising a hydroxyl functional saccharide component and an organosiloxane component were found to be useful when applied to hair, skin, fabric, paper, wood and other substrates. The saccharide component may be covalently bound to the organosiloxane at one or more pendant or terminal positions, or some combination thereof, through linkages including but not limited to ether, ester, and amide bonds. However, the known saccharide siloxanes may suffer from the drawback of losses of performance and/or functionality, especially in aqueous environments.

BRIEF SUMMARY OF THE INVENTION

A saccharide siloxane copolymer (copolymer) has the following formula:

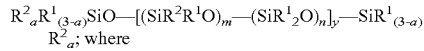
$R^2{}_a R^1{}_{(3-a)}SiO-[(SiR^2R^1O)_m-(SiR^1{}_2O)_n]_y-SiR^1{}_{(3-a)}R^2{}_a$; where each $R^1$ can be the same or different and each $R^1$ comprises hydrogen, an alkyl group of 1 to 12 carbon atoms, an organic group, or a group of formula $R^3$-Q;

Q comprises an epoxy, cycloalkylepoxy, primary or secondary amino, ethylenediamine, carboxy, halogen, vinyl, allyl, anhydride, or mercapto functionality;

subscripts m and n are integers from 0 to 10,000 and may be the same or different; each subscript a is independently 0, 1, 2, or 3;

subscript y is an integer such that the copolymer has a molecular weight less than 1 million;

each $R^2$ has formula Z-$(G^1)_b$-$(G^2)_c$, and there is an average of at least one $R^2$ per copolymer molecule, where $G^1$ is a saccharide component comprising 5 to 12 carbon atoms, a quantity (b+c) has a value ranging from 1 to 10, and subscript b or subscript c can be 0, $G^2$ is a saccharide component comprising 5 to 12 carbon atoms additionally substituted with organic or organosilicon radicals, each Z is a linking group and is independently selected from the group consisting of: —$R^3$—N($R^8$)—C(O)—$R^4$—, —$R^3$—CH(OH)—$CH_2$—N($R^8$)—$R^4$—, or —$R^3$—CH(N($R^4$)($R^8$))$CH_2$OH;

where each $R^3$ and each $R^4$ are divalent spacer groups comprising a group of formula $(R^5)_r(R^6)_s(R^7)_t$, where at least one of subscripts r, s and t is 1, and each $R^5$ and each $R^7$ are independently either an alkylene group of 1 to 12 carbon atoms or a group of formula $(R^9O)_p$, where subscript p is an integer with a value ranging from 1 to 50, and each $R^9$ is a divalent organic group, and each $R^9O$ may be the same or different, each $R^6$ is —N($R^8$)—, where $R^8$ is selected from $R^3$, a group of formula Z—X, an unsaturated hydrocarbon group, or a reaction product of —N(H)— with an epoxy functional group, a cycloalkylepoxy functional group, a glycidyl ether functional group, an acidic anhydride functional group, or a lactone;

each X is independently a divalent carboxylic acid, phosphate, sulfate, sulfonate or quaternary ammonium radical, and with the provisos that at least one of $R^3$ and $R^4$ must be present in the linking group, and each $R^3$ and each $R^4$ may be the same or different.

DETAILED DESCRIPTION OF THE INVENTION

A saccharide siloxane copolymer (copolymer) has improved aqueous stability. The copolymer comprises a saccharide component and a siloxane component. The siloxane component forms the backbone of the copolymer molecule. Saccharide components may be bonded to the siloxane backbone in terminal groups, pendant groups, or both terminal and pendant groups. Alternatively, the saccharide component may be bonded to the siloxane backbone in a pendant group. Without wishing to be bound by theory, it is thought that when the copolymer contains a pendant saccharide component, the copolymer has improved stability in the presence of water as compared to a previously known saccharide siloxane. And, when the copolymer contains pendant saccharide components and no terminal saccharide components, the copolymer may exhibit even further improved stability in the presence of water as compared to a previously known saccharide siloxane, or as compared to a copolymer according to paragraph [0003] having terminal saccharide components and not pendant saccharide components.

The copolymer may be a solid or a fluid under ambient conditions of temperature and pressure, e.g., at 25° C. and 760 mmHg. Whether the copolymer is a solid at ambient conditions, or a fluid such as a liquid or a gum, depends on various factors including the degree of polymerization (DP) of the copolymer. The copolymer may have a DP ranging from 2 to 15000, alternatively 50 to 5,000, alternatively 100 to 1,000, alternatively 50 to 1,000, and alternatively 100 to 400.

The copolymer has the formula: $R^2{}_a R^1{}_{(3-a)}SiO$—$[(SiR^2R^1O)_m$—$(SiR^1{}_2O)_n]_y$—$SiR^1{}_{(3-a)}R^2{}_a$. In this formula, each $R^1$ can be the same or different. Each $R^1$ comprises hydrogen, an alkyl group of 1 to 12 carbon atoms, an organic group, or a group of formula $R^3$-Q. Group Q comprises an epoxy, cycloalkylepoxy, primary or secondary amino, ethylenediamine, carboxy, halogen, vinyl, allyl, anhydride, or mercapto functionality.

Subscripts m and n are integers from 0 to 10,000 and may be the same or different. Each subscript a is independently 0, 1, 2, or 3. Alternatively, each subscript a may be 0. When subscript a is 0, then at least one of subscripts m and n is greater than 0, and all of the saccharide components are in pendant groups (not terminal groups) on the copolymer. Subscript y is an integer such that the copolymer has a molecular weight less than 1 million. Subscript y, and at least one of subscripts m and n, may be greater than 0 such that a saccharide component is in a pendant group on the copolymer.

Each $R^2$ has formula $Z\text{-}(G^1)_b\text{-}(G^2)_c$, and there is an average of at least one $R^2$ per copolymer molecule. Group $G^1$ is a saccharide component comprising 5 to 12 carbon atoms. Subscript b or subscript c can be 0. However, a quantity (b+c) has a value ranging from 1 to 10. Group G is a saccharide component comprising 5 to 12 carbon atoms additionally substituted with organic or organosilicon groups. Substituted means that a hydrogen atom bonded to a carbon atom has been replaced with another substituent, such as with an organic group or an organosilicon group. Each Z is a linking group.

Each Z is independently selected from the group consisting of: —$R^3$—N($R^8$)—C(O)—$R^4$—, —$R^3$—CH(OH)—CH$_2$—N($R^8$)—$R^4$—, or —$R^3$—CH(N($R^4$)($R^8$))CH$_2$OH. Each $R^3$ and each $R^4$ are divalent spacer groups comprising a group of formula $(R^5)_r(R^6)_s(R^7)_t$. At least one of subscripts r, s and t is 1. Each $R^5$ and each $R^7$ are independently either an alkylene group of 1 to 12 carbon atoms or a group of formula $(R^9O)_p$. Subscript p is an integer with a value ranging from 1 to 50. Each $R^9$ is a divalent organic group. Each $R^9O$ may be the same or different. Each $R^6$ is —N($R^8$)—, where $R^8$ is selected from $R^3$, a group of formula Z—X, an unsaturated hydrocarbon group, or a reaction product of —N(H)— with an epoxy functional group, a cycloalkylepoxy functional group, a glycidyl ether functional group, an acetic anhydride functional group, or a lactone. When $R^8$ is an unsaturated hydrocarbon group, $R^8$ may be an alkenyl group. The alkenyl group may have 2 to 12 carbon atoms and is exemplified by vinyl, allyl, decenyl, and dodecenyl. Each X is independently a divalent carboxylic acid, phosphate, sulfate, sulfonate or quaternary ammonium radical. At least one of $R^3$ and $R^4$ must be present in the linking group. Each $R^3$ and each $R^4$ may be the same or different.

The copolymer described above was surprisingly found to have improved stability in aqueous environments as compared to previously known saccharide siloxanes. This benefit makes the copolymer described above particularly useful in personal care compositions. The copolymer described above may also have both improved stability and improved performance in personal care compositions.

DEFINITIONS AND USAGE OF TERMS

The art of "personal care" is intended to include any topical treatment of any portion of the body that is intended to provide a benefit to that portion of the body. The a benefit may be direct or indirect, and may be sensory, mechanical, cosmetic, protective, preventative or therapeutic. While it is contemplated that the human body is a particularly desirable target substrate for the presently disclosed personal care compositions and products formulated therefrom, it will be readily apparent to one skilled in the art that other mammals having similar tissues, especially keratinacious tissue such as skin and hair, may be suitable target substrates and that therefore veterinary applications are within the scope of the present invention.

The personal care compositions, as provided, are adapted to provide a benefit to a portion of the body. As used herein, "adapted" means formulated in a manner that permits safe and effective application of the benefit to the portion of the body. As used herein, "safe and effective" means an amount that provides a level of benefit perceivable by a consumer seeking such a benefit without damaging or causing significant discomfort to the consumer seeking such a benefit. A significant discomfort is one that outweighs the benefit provided such that an ordinary consumer will not tolerate it.

A person of ordinary skill in the personal care formulation arts will appreciate the well-known criterion for selecting the essential ingredients, optional additives and excipients, that are suitable according to the intended application of a particular personal care composition. Non-limiting examples of additives which may be formulated into the personal care compositions in addition to the copolymer include: additional silicones, aerosols, anti-oxidants, cleansing agents, colorants, additional conditioning agents, deposition agents, electrolytes, emollients and oils, exfoliating agents, foam boosters, fragrances, humectants, occlusive agents, pediculicides, pH control agents, pigments, preservatives, biocides, other solvents, stabilizers, sunscreening agents, suspending agents, tanning agents, other surfactants, thickeners, vitamins, botanicals, waxes, rheology-modifying agents, anti-dandruff, anti-acne, anti-carie and wound healing-promotion agents.

It is not uncommon for certain benefits to be sacrificed in personal care products formulated to provide multiple benefits in a single product. For instance, with respect to hair, an increase in conditioning benefit is often accompanied by a decrease in hair "body" or volume. Addition of the copolymer may permit the formulation of products which combine such benefits without sacrificing the efficacy of some, and, indeed, in some formulations it provides synergy with respect to the combination of benefits. Personal care products formulated from the personal care compositions comprising the copolymer described herein may provide enhancements in benefits which typically derive from effects which antagonize one another, for example, enhancing both conditioning and curl retention benefits. They also may provide thickening benefits in hair, skin, and color cosmetics.

In addition, the addition of the copolymer described herein to personal care compositions may eliminate or lessen the need for certain other additives. For example, because of the increased hydrogen bonding properties of the copolymer described herein, it is an effective thickening agent for cyclic silicones such as cyclomethicone and may therefore lessen the need for other thickening additives which may incidentally confer undesirable product properties such as stringency, residue formation and/or conditioning defects.

The copolymer described herein may be a gum, waxy solid or solid at ambient conditions. It should be noted, however, that there is a subset of the copolymer that exists in a liquid form, and liquid dispersible forms may also be produced by manipulating conditions such as temperature. However, for some copolymers to achieve a viscosity range that permits ready formation of dispersions, for example solutions or emulsions, the copolymer must first be solubilized by being dissolved in a suitable solvent or solvent blend.

The solubilized copolymer is then used to form a solution or emulsion for ready delivery into the personal care composition. The particular solvent blend is selected based upon the ionic properties of the copolymer, and the suitability of that solvent for the intended application. In one specific embodiment the solvent blend comprises a mixture of paraffin and an alcohol. In a very specific embodiment the alcohol comprises isopropyl alcohol, 2-butyl-octanol, or a combination thereof. Alternatively, the alcohol may comprise 2-butyl-octanol.

The term "dispersion" as used herein means a two-phase system where a first phase comprises finally divided particles distributed throughout a bulk second phase and the first phase constitutes an "internal" or dispersed phase while the second phase constitutes an "external" or continuous phase.

The term "solution" as used herein is intended broadly to include mechanical dispersions, colloidal dispersions and true solutions, and should not be construed as limited to the latter. A solution is a dispersion comprising a uniformly dispersed mixture wherein a first phase constitutes the solute and a second phase constitutes the solvent.

The term "emulsion" as used herein means a dispersion comprising a mixture of two immiscible liquids with the liquid constituting the first, dispersed internal phase being suspended in the second, continuous phase with the aid of an emulsifier.

All amounts, ratios, and percentages are by weight unless otherwise indicated. As used herein, the articles 'a' 'an' and 'the' each refer to one or more, unless otherwise indicated by the context of the application.

Composition

The copolymer described above may be formulated in a composition. The composition comprises (A) a copolymer described above in paragraph [0003], and (B) an additional ingredient. The additional ingredient depends on the specific copolymer selected and the desired end use for the composition.

The composition may be a personal care composition. The personal care composition may comprise: (i) the copolymer described above in paragraphs [0003] to [0010], and optionally (ii) a carrier medium suitable to permit topical application of the personal care composition to a portion of the body. The personal care composition is adapted to provide a benefit to the portion of the body to which it is applied. In addition, the personal care composition may optionally comprise (iii) a cross-linker, which acts to cross-link among the copolymer(s) and/or with the substrate to which the composition is applied. The personal care composition may optionally comprise (iv) a surfactant.

Cross-linkers suitable for crosslinking the copolymer are known in the art. In specific embodiments, the crosslinking substantially occurs between the hydroxy-functional groups of the saccharide components. In more specific embodiments the cross-linker may be selected from the following non-limiting list: boric acid, borate ester (e.g., tri-n-propyl borate, triisopropanolamine borate), alkyl boronic acid or ester (e.g., phenyl boronic acid), titanate, (e.g., titanium isopropoxide, diisopropoxytitanium bis(acetylacetonate)), zirconate, glyoxal, glutaraldehyde, epichlorohydrin, urea-formaldehyde, zirconium ammonium carbonate, salt of a multivalent ion, bifunctional epoxy or glycidyl compounds (e.g., 1,4 butanediol diglycidyl ether), di-(N-hydroxymethyl)urea, di-isocyanate (e.g., toluene diisocyanate, hexamethylene diisocyanate), 2-chloro N,N di-ethylacetamide, sodium trimetaphosphate, phosphorous oxychloride, acrolein, N-methyl urea, dicarboxylic acid, bis-acid chloride, dialkyldichlorosilane (e.g., dimethyldichlorosilane), alkyltrichlorosilane (e.g., methyltrichlorosilane), reactive siloxane resin, and combinations thereof. In a very specific embodiment, the cross-linker comprises a reactive siloxane resin or boronic acid or ester.

Alternatively, the copolymer may be delivered to the personal care composition as a dispersion. Diluting or dispersing the copolymer makes it easier to process, and suitably employable solvents include polydimethylsiloxanes, hydrocarbons, and alcohols. Particularly suitable solvents are cyclic siloxanes, hydrocarbon-alcohol mixtures, linear long chain alcohols and branched long chain alcohols, and water.

Due to the compatibility of the copolymer with hydrocarbons, silicones and alcohols, as well as with water, they may be incorporated into both aqueous and non-aqueous based personal care products, which provide a benefit to the portion of the body. In embodiments where the portion of the body comprises hair, the benefit may include increased ease and hold of hair-styling, fixative effects and shine-enhancement.

Methods for Making Compositions

The copolymers may be formulated into a composition in a substantially pure form, or as a dispersion in the form of either a solution or an emulsions. Depending on the form used, the copolymer may be formulated into oil in water, water in oil, water in silicone and silicone in water systems. In the case of some aqueous-based formulations the saccharide-siloxane may be added directly to the formulation as a solid. In one embodiment, the dispersion is in the form of a solution. The solvent may be substantially aqueous or substantially non-aqueous depending on the desired end use of the composition. In a specific embodiment the substantially non-aqueous solvent comprises a volatile or non-volatile solvent and in a very specific embodiment the substantially non-aqueous solvent comprises a volatile hydrocarbon or a silicone or mixtures thereof. In a more specific embodiment the substantially non-aqueous solvent comprises a silicone.

The term "volatile" as used herein means that the solvent exhibits a significant vapor pressure at ambient conditions. Examples of suitable volatile silicones include siloxanes such as phenyl pentamethyl disiloxane, phenylethylpentamethyl disiloxane, hexamethyldisiloxane, methoxy propylheptamethyl cyclotetrasiloxane, chloropropyl pentamethyl disiloxane, hydroxypropyl pentamethyl disiloxane, octamethyl cyclotetrasiloxane, decamethyl cyclopentasiloxane and mixtures thereof. Particularly suitable silicones are the cyclomethicones. In a very specific embodiment the volatile silicone comprises a cyclic siloxane.

The copolymer ingredient is typically added to the personal care composition as a dispersion. Because of this, one may describe its concentration with respect to either the dispersion component or the personal care composition as a whole. In one embodiment wherein the personal care composition comprises a dispersion, the dispersion comprises from 0.1% to 50% copolymer by weight percent and from 0.01% to 25% copolymer by weight percent of the composition. In a more specific embodiment the dispersion comprises from 2% to 40% copolymer by weight percent and from 0.2% to 10% copolymer by weight percent of the composition. In an even more specific embodiment the solution comprises 20% copolymer by weight percent and 0.5 to 2% copolymer by weight of the composition.

In one embodiment of the personal care composition, the dispersion is in the form of an emulsion. The emulsion additionally comprises a surfactant to maintain the dispersion, and water as the continuous phase. The internal phase comprises the dispersed solubilized copolymer. Nonionic, amphoteric (including zwitterionic), anionic or cationic surfactants may all be suitable. Oil in water emulsions are typically used because they are easier to handle and disperse readily into water-based formulations.

An additional embodiment of the present invention is directed to a copolymer emulsion. The emulsion is an oil in water emulsion comprising an internal phase comprising the copolymer and a continuous phase comprising water. The copolymer emulsion comprises a surfactant which maintains the dispersion of the internal phase due to its amphipathic character.

An additional embodiment of the present invention is directed to the continuous phase of the oil in water emulsion. The pH of the continuous phase can be adjusted with acids and bases. In these cases, enhanced elevated temperature stability has been shown after neutralizing the emulsion. The preference is to use natural acids such as acetic acid or citric acid. Other acids include arachidonic acid, ascorbic acid, benzoic acid, capryloyl salicylic acid, coconut acid, corn acid, cottonseed acid, dehydroacetic acid, dilinoleic acid, erythorbic acid, formic acid, fumaric acid, gluconic acid, glutamic acid, glycolic acid, glycyrrhetinic acid, glycyrrhizic acid, hyaluronic acid, hydrogenated coconut acid, hydroxystearic acid, isostearic acid, lactic acid, lanolin acid, lauric acid, linoleic acid, maleic acid, malic acid, myristic acid, oleic acid, olive acid, palmitic acid, pantothenic acid, pca, peanut acid, pentetic acid, phosphoric acid, picramic acid, polyglutamic acid, propionic acid, rice bran acid, ricinoleic acid, salicylic acid, sorbic acid, soy acid, stearic acid, sunflower seed acid, tall oil acid, tartaric acid, trilinoleic acid, undecylenic acid, urocanic acid, alpha hydroxyl acids, 2-hydroxyoctanoic acid, 2-hydroxydecanoic acid, alpha lipoic acid, but nearly any proton donator is acceptable for lowering the pH.
Addition to Examples Example 14

Polymer Emulsification, Speed Mixer

A copolymer (47.5 grams) from the examples above was blended with Isofol 12 (2-butyloctanol) from Sasol Co. (2.5 grams), and further blended with Tergitol 15-s-3 (which is a secondary ethoxylated (~3) alcohol with 11 to 15 carbon atoms) from the Dow Chemical Company of Midland, Mich., USA (1.0 grams) via a Hauschild Engineering Speed Mixer (Model # DAC 150 FZ) with a speed of 3500 rpm for 15 seconds in a max 100 g cup. Tergitol 15-s-40 (a secondary ethoxylated (~40) alcohol with 11 to 15 carbon atoms, 70% concentration in water) also from Dow Chemical Company (5.5 grams) and de-ionized water (4.5 grams) were added and immediately subjected to high levels of mixing shear as provided by the Speed Mixer. Typically, 4 cycles of mixing at 3500 rpm for 25 seconds each followed by mixer cup scraping were needed to fully transition the mixture to an oil-in-water configured emulsion. Subsequent incremental additions of de-ionized water (totaling 39.0 grams) were also completed using the Speed Mixer. Post additions of preservatives into the water phase were made, consisting of Phenoxetol—Low Phenol (Phenoxyethanol) from Clariant (0.9 grams) and Neolone 950 (methylisothiazolinone, 9.5% in water) from Rohm and Haas (0.079 grams). Some emulsified saccharide siloxane co-polymers yield either an acidic or basic solution. In these cases, enhanced elevated temperature stability has been shown after neutralizing the emulsion. The preference is to use natural acids such as citric or acetic, but nearly any proton donator is acceptable for lowering the pH. For raising measured pH values, hydroxyl ion donating substances or various other bases can be incorporated. The neutralizing agent used should be suitable for the final application of the emulsion. All mixing was completed at atmospheric pressure and at room temperature with some heat being generated during the inversion step observed to be approximately 40° C. The resulting product was an oil in water emulsion with a mono-modal particle size distribution having a volume average particle diameter of 300.0 nanometers as measured by a Malvern particle size analyzer (model # MS-S). The product had a Non-Volatile Content (NVC) of 55% by weight by subjecting two grams of emulsion to 105° C. for two hours.

Example 15

Polymer Emulsification, Change Can Mixer

One of several variations of a saccharide siloxane copolymer (2042.5 grams) prepared in the above examples was blended with Isofol 12 (2-butyloctanol) from Sasol Co. (107.5 grams) and was further blended with Tergitol 15-s-3 (C11-C15 secondary ethoxylated (~3) alcohol) from Dow Chemical Company (42.8 grams) via a Ross change can mixer equipped with 2 disperser blades and an anchor style scraper blade commonly called a tri-shaft design (Model # VMC-1) with a speed of 40 rpm on the scraper blade for 3 minutes. Tergitol 15-s-40 (C11-C15 secondary ethoxylated (~40) alcohol, 70% concentration in water) from Dow Chemical Company (236.8 grams) and de-ionized water (100.9 grams) were added and immediately subjected to high levels of mixing shear as provided by the Ross Mixer. Typically 2 cycles of mixing at 4000 rpm on the disperser blades and 40 rpm on the scraper blade for 3 minutes each followed by mixer scraping with a spatula of both the blades and pot were needed to fully transition the mixture to an oil-in-water configured emulsion. Subsequent incremental additions of de-ionized water (totaling 1727 grams) were also completed using the Ross Mixer. Post additions of preservatives were made into the water phase, consisting of Phenoxetol—Low Phenol (Phenoxyethanol) from Clariant (38.7 grams) and Neolone 950 (methylisothiazolinone, 9.5% in water) from Rohm and Haas (3.4 grams). Some emulsified saccharide siloxane co-polymers yield either an acidic or basic solution. In these cases, enhanced elevated temperature stability has been shown after neutralizing the emulsion. The preference is to use natural acids such as citric or acetic, but nearly any proton donator is acceptable for lowering the pH. For raising measured pH values, hydroxyl ion donating substances or various other bases can be incorporated. The neutralizing agent used should be suitable for the final application of the emulsion. All mixing was completed under vacuum at a level of 20 in Hg to minimize foaming. Natural heat was generated during the inversion step and cooling was utilized on the mixer pot jacket to maintain temperature below 40° C. The resulting product was an oil in water emulsion with a mono-modal particle size distribution having a volume average particle diameter of 300.0 nanometers as measured by a Malvern particle size analyzer (model # MS-S) and with a Non-Volatile Content (NVC) of approximately 55% by weight by subjecting two grams of emulsion to 105° C. for two hours.

Other embodiments provide methods for preparing the emulsions. The copolymer emulsions may be prepared either by: 1) emulsifying preformed copolymers or 2) by polymerizing monomers into a higher molecular weight copolymer in each individual emulsion particle e.g., via emulsion or suspension polymerization. In one embodiment, a surfactant-water blend is added to a solubilized copolymer first in order to establish the dispersion and fix the water phase. Optional additional portions of water are added as required by the desired property profile of the emulsion and/or its intended applications.

It will be understood by one of ordinary skill in the art that there is a continuum for the ease with which a desired emulsion forms. Copolymer emulsions share similar constraints with other emulsions. That is, they are thermodynamically unstable, require a surfactant to maintain the dispersion, and need an input of energy to initiate emulsification. Simple agitation via mixing may be sufficient, or higher shear means including the employment of high shear devices may be required. In other instances, a polymer emulsification or inversion method may be needed.

A degree of agitation necessary to form the emulsion may require employment of mixing devices. Mixing devices typically provide the required energy input. Non-limiting examples of these mixing devices spanning the shear range include: 1) a vessel with an impeller, for example, propeller, pitched blade impeller, straight blade impeller, Rushton impeller, or Cowles blade; 2) kneading type mixers, for example, Baker-Perkins; 3) high shear devices which use positive displacement through an orifice to generate shear, for example, homogenizer, sonolator, or microfluidizer; 4) high shear devices using a rotor and stator configuration, for example, colloid mills, homomic line mills, IKA, or Bematek; 5) continuous compounders with single or dual screws; 6) change can mixers with internal impellers or rotor/stator devices, for example, Turello mixer; and 7) centrifugal mixers, for example, Hauschild speedmixers. Combinations of mixing devices can also provide benefits, for example a vessel with an impeller can be connected to a high shear device.

The choice of mixing device is based on the type of internal phase to be emulsified. For example, low viscosity internal phases can be emulsified using high shear devices which use positive displacement through an orifice. However, in the case of high viscosity internal phases, a rotor/stator device, twin screw compounder or change can mixer are often better choices. In addition, internal phases that contain hydrophilic groups are often easier to emulsify and therefore a simple vessel configured with an impeller may be sufficient.

The viscosity of the copolymer depends on various factors including the molecular weight of the siloxane portion, the number of saccharide units, the mole percent of saccharide units per siloxane, and the external conditions such as temperature and pressure. One skilled in the art would recognize that variable internal phase viscosities may be achieved by varying proportions in blends of copolymers with solvents or solvent mixtures.

The most desirable order of ingredient addition in the preparation of the emulsion is determined empirically. For example, a desirable order of addition for a thick-phase emulsification may be: (a) solubilize the copolymer in a solvent or solvent blend to a desired viscosity; (b) blend in a surfactant; (c) add water in increments with shear until a thick phase emulsion forms; (d) dilute with water to desired concentration, with shear. A desirable order of addition for a "pre-mix" with high shear may be: (a) add all the water to a mixing vessel configured with an impeller; (b) blend a surfactant with the water; (c) slowly add the copolymer phase to the water to make a rough emulsion; (d) convey the rough emulsion through a high shear device until a desired particle size is achieved.

Nonionic surfactants are suitable for making the emulsions and include alkyl ethoxylates, alcohol ethoxylates, alkylphenol ethoxylates, and mixtures thereof. Cationic, amphoteric and/or anion surfactants are also suitable and are typically added in addition to a nonionic surfactant. In a specific embodiment the emulsion comprises a nonionic surfactant and in another specific embodiment the emulsion comprises a cationic surfactant and a nonionic surfactant.

In one embodiment of the personal care composition wherein the copolymer is delivered to the composition in the form of an emulsion, the emulsion comprises 5% to 95% copolymer by weight percent of the emulsion and the composition comprises 0.01% to 25% saccharide-siloxane by weight percent of the composition. In a more specific embodiment the emulsion comprises 10% to 60% copolymer by weight percent of the emulsion and from 0.2% to 10% copolymer by weight percent of the composition. In an even more specific embodiment the solution comprises 20 to 50% copolymer by weight percent and 0.5 to 2% copolymer by weight of the composition.

The personal care compositions comprising the copolymer may be formulated into personal care products. The personal care products may be functional with respect to the portion of the body to which they are applied, cosmetic, therapeutic, or some combination thereof. Conventional examples of such products include, but are not limited to: antiperspirants and deodorants, skin creams, skin care lotions, moisturizers, facial treatments such as acne or wrinkle removers, personal and facial cleansers, bath oils, perfumes, colognes, sachets, sunscreens, pre-shave and after-shave lotions, shaving soaps, and shaving lathers, hair shampoos, hair conditioners, hair colorants, hair relaxants, hair sprays, mousses, gels, permanents, depilatories, and cuticle coats, make-ups, color cosmetics, foundations, concealers, blushes, lipsticks, eyeliners, mascara, oil removers, color cosmetic removers, wrinkle fillers, skin imperfection hiders, skin surface smoothers, eyelash curlers, nail varnishes, hair make-up products, eye shadows, body makeups, and powders, medicament creams, pastes or sprays including anti-acne, dental hygienic, antibiotic, healing promotive, nutritive and the like, which may be preventative and/or therapeutic. In general the personal care products may be formulated with a carrier that permits application in any conventional form, including but not limited to liquids, rinses, lotions, creams, pastes, gels, foams, mousses, ointments, sprays, aerosols, soaps, sticks, soft solids, solid gels, and gels. What constitutes a suitable carrier is readily apparent to one of ordinary skill in the art.

In some personal care product embodiments comprising the inventive personal care composition, inclusion of the copolymer decreases the need for other thickening agents in the formulation. In these embodiments, desired viscosity or thickness of the product is maintained with a lesser amount than is typical of conventional thickeners. This is particularly desirable in products wherein the thickening agent antagonizes a desirable effect of another benefit agent, such as, for example, a conditioning agent. It is also desirable in products where one or more thickening agents are included for processing or formulation characteristics rather than for any desired benefit they provide to the portion of the body to which they are applied. In these cases, the copolymer may permit a decrease in the one or more thickening agents that possess antagonistic performance characteristics.

In some personal care product embodiments comprising the inventive personal care composition, inclusion of the copolymer decreases the need for water in oil, and more specifically water in silicone emulsifiers. The copolymer itself may provide emulsification properties. In these embodiments, desired emulsification of the product is maintained with a lesser amount than is typical of conventional water in silicone emulsifiers.

In a specific embodiment of the personal care product comprising the personal care composition, the benefit comprises a conditioning benefit and the portion of the body comprises hair. Specific examples of the conditioning benefit include, but are not limited to an anti-static, lubricity, shine, viscosity, tactile, manageability, or a styling benefit. Non-limiting examples of manageability benefits include ease of dry and/or wet combing. Non-limiting examples of styling benefits include curl retention or hair-relaxing benefits. The conditioner may be a rinse-off or leave-in conditioner. In a specific embodiment the conditioning benefit comprises a curl-retention benefit.

Examples of suitable conditioning agents include, but are not limited to, cationic polymers, cationic surfactants, proteins, natural oils, silicones other than the copolymer, hydrocarbons, nonionic surfactants, amphoteric surfactants, or mixtures thereof. Examples of additional silicones which may be useful in the present personal care compositions include, but are not limited to: alkyl methyl siloxanes, cyclic siloxanes, gums, linear siloxanes, MQ siloxane resins, MTQ siloxane resins, and polyether siloxane copolymers.

Further embodiments of the present invention are direct to methods for providing a benefit to a portion of the body. One such method comprises administration of a safe and effective amount of a personal care product comprising the inventive personal care composition to a portion of the body. In one specific embodiment, a method of treating hair comprising administering a safe and effective amount of the novel personal care composition is provided. A very specific embodiment provides a method of styling and holding hair comprising administering a safe and effective amount of the novel personal care composition. As used herein, "safe and effective" means an amount that provides a level of benefit perceivable by a consumer seeking such a benefit without damaging or causing significant discomfort to the consumer seeking such a benefit. A significant discomfort is one that outweighs the benefit provided such that an ordinary consumer will not tolerate it.

Formulating personal care products with the personal care composition comprising the copolymer as described above provides a thickening benefit. In a specific embodiment, an antiperspirant, hair, skin and color cosmetic products are provided. The antiperspirant product is formulated with the personal care composition comprising the copolymer as described above, wherein the benefit comprises a thickening benefit sufficient to maintain suspension of antiperspirant salts when the formulation comprises a substantially less than typical amount of conventional thickeners. In specific embodiments, the antiperspirant product is provided in the form of a solid, a soft solid or a gel. In a more specific embodiment the solid form comprises a soft solid or a gel.

Another specific embodiment of the present invention is directed to an emulsification benefit for water in oil and more specifically, water in silicone formulations. The amount of water in silicone formulation aids needed may be lower than typical when the copolymer is used in the formulation. In a more specific embodiment an antiperspirant product is formulated with the composition comprising the copolymer. In an even more specific embodiment the solid form comprises a gel.

Another specific embodiment provides a personal care product comprising the novel personal care composition where the benefit comprises an enhanced conditioning benefit and the portion of the body comprises skin. An embodiment directed to a method of treating skin is provided which comprises: (1) administration of a safe and effective amount of the personal care product comprising the novel personal care composition; and (2) rubbing the safe and effective amount into the skin.

Another specific embodiment is directed to a color cosmetic product comprising the novel personal care composition where the benefit comprises a cosmetic benefit. More specific embodiments are directed to liquid foundations.

Methods for Making the Saccharide Siloxane Copolymer

A copolymer described in paragraphs [0003] to [0010] may be made by a method comprising:
1) reacting an amine functional polyorganosiloxane containing a primary amine and a secondary amine with a sugar lactone to consume the primary amine,
2) reacting the product of step 1) with a capping agent to block the secondary amine. The secondary amine functionality may be selected from aminoethylaminopropyl, and aminoethylaminoisobutyl. The sugar lactone may be an aldonolactone or another lactone derived from a saccharide. Aldonolactones are lactones derived from aldonic acids. The capping agent may be a lactone, a halogenated unsaturated compound, an epoxy functional compound, or an acid anhydride.

Step 1) may be performed by reacting (A) an amino-functional polyorganosiloxane and (B) an aldonolactone. Ingredient (A) may have the formula:

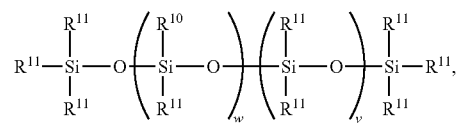

where each $R^{10}$ is a independently secondary amino group; each $R^{11}$ is independently a monovalent hydrocarbon group or $R^{10}$; subscript w has a value ranging from 0 to 10,000, and subscript v has a value ranging from 0 to 10,000, with the proviso that when all instances of $R^{11}$ are monovalent hydrocarbon groups, then subscript w is greater than 0. The secondary amino group may be, for example, aminoethylaminoisobutyl or aminoethylaminopropyl.

Ingredient (A) is exemplified by trimethylsiloxy-terminated poly(dimethylsiloxane/methyl(aminoethylaminoisobutyl)siloxane), trimethylsiloxy-terminated poly(dimethylsiloxane/methyl(aminoethylaminopropyl)siloxane), and combinations thereof. Ingredient (B) is an aldonolactone or another lactone derived from a saccharide. The aldonolactone suitable for ingredient (B) is exemplified by gluconolactone (GL), erythronolactone, galactonolactone, gluconolactone, mannonolactone, and ribolactone. Other lactones derived from saccharides can include glucoronolactone, glucoheptanolactone, glucooctanolactone, isocitric acid lactone, saccharolactone, and lactobionolactone (LBL). Alternatively, ingredient (B) may be GL or LBL. Lactones suitable for ingredient (B) are commercially available.

Step 2) may be performed by reacting the product of step 1) with (C) a capping agent to block the secondary amine. The capping agent may be a lactone, a halogenated unsaturated compound capable of reacting with the hydrogen on the secondary amine functionality, an epoxy functional compound, or an acid anhydride.

The capping agent may be a lactone. The lactone may have the formula:

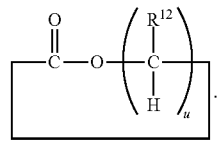

Each $R^{12}$ is independently a hydrogen atom, a hydroxyl group, an alkoxy group, or a saccharide group. Alkoxy groups are exemplified by methoxy, ethoxy, propoxy, and butoxy. Alternatively, each $R^{12}$ is a hydroxyl group or a saccharide group. Subscript u has a value ranging from 5 to 12. The lactone used in step 2) may be exemplified by the sugar lactones described above. Alternatively, the lactone may be butyrolactone, epsilon caprolactone, gamma gluconolactone, delta gluconolactone, and LBL. Alternatively, the lactone may be gamma gluconolactone or delta gluconolactone.

Alternatively, the capping agent may be halogenated unsaturated compound capable of reacting with the hydrogen atom on the secondary amine. The halogenated unsaturated compound may be a halogenated unsaturated hydrocarbon such as an alkenyl chloride. Suitable alkenyl chlorides may have 2 to 12 carbon atoms and may include vinyl chloride, allyl chloride, decyl chloride, or dodecyl chloride.

Alternatively, the capping agent may be an epoxy functional compound. The epoxy functional compound may be selected from allyl epoxy functional compounds, cycloalkylepoxy functional compounds, glycidyl ether functional compounds, and glycidol.

Alternatively, the capping agent may be an acidic anhydride. The acid anhydride may have the formula:

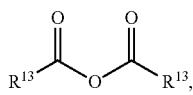

where each $R^{13}$ is independently a monovalent hydrocarbon group. Alternatively, each $R^{13}$ may be an alkyl group, such as an alkyl group of 1 to 12 carbon atoms. Suitable alkyl groups are represented by methyl, ethyl, propyl, and butyl. Alternatively, the acid anhydride may comprise acetic anhydride, chloroacetic anhydride, propionic anhydride, crotonic anhydride, methacrylic anhydride, butyric anhydride, isobutyric anhydride, diethyl pyrocarbonate, or 4-pentenoic anhydride. Alternatively, the acid anhydride may be acetic anhydride.

Alternatively, a copolymer according to paragraph [0003] may be prepared by a method comprising reacting an epoxy functional polyorganosiloxane with an n-alkyl glucamine such as n-methyl glucamine. The epoxy functional polyorganosiloxane may be prepared by methods known in the art, such as by hydrosilylation of ingredients comprising an alkenyl functional epoxy containing compound and a polyorganohydrogensiloxane. The alkenyl functional epoxy containing compound may be allyl glycidyl ether, dodecenyl glycidyl ether, tetradecenyl glycidyl ether, or octadecenylglycidyl ether. The ingredients may optionally further comprise further comprise an alkene, such as undecene. Alternatively, one skilled in the art could react the n-alkyl-glucamine first with the alkenyl functional epoxy containing compound and thereafter perform the hydrosilylation reaction to attach the product thereof to the polyorganohydrogensiloxane.

The methods described above may be performed neat or in the presence of a solvent. The solvent may be a carrier medium as described above or a solvent such as that described in paragraphs [0017] to [0026]. Alternatively, the amine functional polyorganosiloxane, or epoxy functional polyorganosiloxane, may be dissolved in ethanol with the other ingredients used in the method. All or a portion of the solvent may be removed, for example, by stripping or distillation, after the method is complete. Alternatively, the copolymer may be left in the solvent after the method is complete, for example, if the solvent is a suitable carrier medium for a composition in which the copolymer will be formulated.

The methods described above may be performed by heating. The exact temperature depends on various factors including the specific ingredients selected, however, temperature may range from 50° C. to 100° C. and reaction time for each step may be several hours, alternatively, up to 10 hours, alternatively 1 to 10 hours. The first and second steps in the methods described above may be performed sequentially. Alternatively, step 1 and step 2 may be combined and performed simultaneously.

In the methods described above a molar excess may be used of the functionality on the reagent reacting with the functionality on the polyorganosiloxane. For example, in the hydrosilylation of allyl glycidyl ether with an SiH intermediate polyorganosiloxane, a 1.1:1 ratio is used of the moles allyl glycidyl ether to the moles of SiH. The ratio for the reagent to siloxane bonded functionality may be as large as 1.8:1. Alternatively, the molar ratio may range from 1:1 to 1.8:1, alternatively 1.1:1 to 1.5:1.

Alternatively, the molar ratio of sugar lactone to amine may be 1:1, calculated from amine value of the amine functional polyorganosiloxanes. However, the molar ratio of sugar functionality in the sugar lactone to amine in the amine functional polyorganosiloxane may range from 0.5:1 to 2.0:1.

EXAMPLES

The following examples are included to demonstrate the invention to one of ordinary skill. However, those of ordinary skill in the art should, in light of the present disclosure, appreciate that many changes can be made in the specific embodiments which are disclosed and still obtain a like or similar result without departing from the spirit and scope of the invention. All amounts, ratios, and percentages are by weight unless otherwise indicated.

The following ingredients were used in the examples. GL refers to gluconolactone. AGE refers to allyl glycidyl ether. DGE refers to dodecylglycidyl ether. ACL refers to allyl chloride. DCL refers to decyl chloride or 1-chlorodecane. AA refers to acetic anhydride. GLY refers to glycidol. IPA refers to isopropanol. Pt IV refers to a platinum catalyst in which Pt is complexed with divinyltetramethyldisiloxane, also known as Karstedt's catalyst.

Example-1a

Secondary Amine of Aminoethylaminoisobutyl Reacted with AGE

DOW CORNING® Q2-8175 Fluid (Dow Corning Corp., Midland, Mich.), a 150-400 cst. polydimethylsiloxane with pendant aminoethylaminoisobutyl groups (approximately 2.3 mole percent), was reacted with gluconolactone under the following conditions. First, 250 g of a reaction mixture was prepared by reacting DOW CORNING® Q2-8175 Fluid having an amine value of 0.51 meq/g with 11.36 g gluconolactone in ethanol solvent at 74° C. until the amine value reached to 0.25±0.05 meq/g to make the polymer/ethanol reaction mixture. In the second step, 2.05 g AGE was added to 250 g of the polymer/ethanol reaction mixture (~50% concentration). The molar ratio of secondary amine in the polymer to AGE was 1.0:0.5. The reaction was continued at 75° C. for 8 to 12 hours. Proton Nuclear Magnetic Resonance (H-NMR) was used to confirm the completion of reaction. Ethanol solvent was then stripped under vacuum. The resulting copolymer was characterized by NMR, and dynamic viscosity was checked on an ARES Rheometer.

Example-1b

Secondary Amine of Aminoethylaminoisobutyl Reacted with AGE

An trimethylsiloxy-terminated amine functional polydimethylsiloxane, which had DP of 350 and contained 2 pendant aminoethylaminoisobutyl functionalities, (300 g) was reacted with gluconolactone (4.14 g) in ethanol solvent at 74° C. for 6 hours. The amine content in the polymer after the reaction reduced from 0.155 to 0.076 meq/g. H-NMR confirmed the consumption of primary amines of the polyorganosiloxane by gluconolactone through amide linkage. In the second step, 1.35 g AGE was added to 250 g of the reaction mixture (60.3% concentration) and reacted at 74° C. for 9 hours. Ethanol solvent was stripped. The resulting copolymer was characterized by NMR, which confirmed reaction of the secondary amine with the epoxy ring.

Example-1c

Secondary Amine of Aminoethylaminoisobutyl Reacted with AGE

A trimethylsiloxy-terminated, secondary amine functional polydimethylsiloxane, which had DP of 375 and contained four pendant aminoethylaminoisobutyl functionalities, (200 g) was reacted with 4.9 g GL and 3.14 g AGE in-situ in ethanol solvent at 74° C. in a 1 liter flask. Although the gluconolactone reaction was complete in 4 hours, only half of the AGE reacted with secondary amine. Extra AGE (3.2 g) was added to the reaction mixture and reacted for 6 hours. Proton NMR showed complete reaction of secondary amines. Ethanol solvent was stripped from the product under vacuum. The resulting copolymer was characterized by NMR, and room temperature rheology was tested.

Example-1d

Secondary Amine of Aminoethylaminoisobutyl Reacted with AGE

In the first step, a trimethylsiloxy terminated, amine-functional polydimethylsiloxane having a DP of 400 and 8 pendant aminoethylaminoisubutyl functional groups per molecule was synthesized by reacting 13.67 g gluconolactone with 250 g of an aminosiloxane having an amine value of 0.61 meq/g. The reaction was performed in ethanol solvent at 74° C. for 3 to 5 hours until the amine value reached 0.30±0.04. In the second step, 8.94 g AGE was added to the reaction mixture and reacted at 74° C. for 5 to 8 hours. Ethanol solvent was stripped. The resulting copolymer was characterized by NMR, and frequency sweep dynamic viscosity was checked on an ARES Rheometer.

Example-1e

Comparative

DOW CORNING® Q2-8175 Fluid (Dow Corning Corp., Midland, Mich.), a 150-400 cst. polydimethylsiloxane with pendant aminoethylaminoisobutyl groups (approximately 2.3 mole percent), was reacted with gluconolactone under the following conditions. First, 250 g of a reaction mixture was prepared by reacting DOW CORNING® Q2-8175 Fluid having an amine value of 0.51 meq/g with 11.36 g gluconolactone in ethanol solvent at 74° C. until the amine value reached to 0.25±0.05 to make the polymer/ethanol reaction mixture. Ethanol solvent was then stripped under vacuum. The resulting copolymer was characterized by NMR, and dynamic viscosity was checked on an ARES Rheometer.

Example-2a

Secondary Amine of Aminoethylaminoisobutyl Reacted with DGE

The first step was the same as in example 1a. However, instead of using AGE, in the second step, 5.28 g dodecylglycidylether (DGE) was added to 246 g of the reaction mixture (~50% concentration). The molar ratio of secondary amine to DGE was 1.0:0.5. The reaction was continued at 75° C. for 8 hours. H-NMR was used to confirm the completion of reaction. Ethanol solvent was then stripped under vacuum. The resulting copolymer was characterized by NMR, and dynamic viscosity was checked on ARES Rheometer.

Example-2b

Secondary Amine of Aminoethylaminoisobutyl Reacted with DGE

A trimethylsiloxy-terminated polydimethylsiloxane with a DP of 350, which contained 2 pendant aminoethylaminoisobutyl functionalities (300 g), was reacted with gluconolactone (4.14 g) in 200 g ethanol solvent at 74° C. for 6 hours. The amine content in the polymer after the reaction reduced from 0.155 to 0.074 meq/g. H-NMR confirmed the consumption of primary amines by gluconolactone through amide linkage. In the second step, 3.31 g DGE was added to 246 g of the reaction mixture (60.3% concentration) and reacted at 74° C. for 8 hours. The secondary amine reacted with DGE by opening up the epoxy ring. Ethanol solvent was stripped. The resulting copolymer was characterized by NMR.

Example-3a

Secondary Amine of Aminoethylaminoisobutyl Reacted with ACL

First, 300 g of DOW CORNING® Q2-8175 Fluid was reacted with 14.0 g gluconolactone. The reaction was performed in ethanol solvent at 60% concentration at 74° C. until the amine value decreased from 0.51 meq/g to 0.25±0.05 to form a reaction mixture. In the second step, 3.80 g allyl chloride (ACL) was added to 313 g of the reaction mixture (~60% concentration). The molar ratio of secondary amine to ACL was 1.0:1.0. The reaction was continued at 55° C. for 2 hours and 74° C. for 9 hours. H-NMR was used to confirm the completion of reaction. Ethanol solvent was then stripped under vacuum. The resulting copolymer was characterized by NMR, and dynamic viscosity was checked on an ARES Rheometer.

Example-3b

Secondary Amine of Aminoethylaminoisobutyl Reacted with ACL

First, 300 g of a trimethylsiloxy-terminated, secondary amine functional polydimethylsiloxane with DP of 375, and which contained four pendant aminoethylaminoisobutyl functionalities, was reacted with 7.35 g gluconolactone in 200 g ethanol solvent at 74° C. in a 1 liter flask. The reaction was complete in 3 hours as evident from H-NMR. Second, 270 g of the reaction mixture was charged in a separate flask and reacted with 3.14 g allylchloride at 55° C. for 2 hours and 74° C. for 13 hours. H NMR showed complete reaction of secondary amines. Ethanol solvent was stripped from the product under vacuum. The resulting copolymer was characterized by NMR and room temperature rheology was tested.

Example-4a

Secondary Amine of Aminoethylaminoisobutyl Reacted with AA

DOW CORNING® Q2-8175 Fluid (Dow Corning Corp., Midland, Mich.), a 150-400 cst. polydimethylsiloxane having the amine value of 0.51 meq/g with pendant aminoethylaminoisobutyl groups (approximately 2.3 mole percent), was reacted with gluconolactone under the following conditions. First, a reaction mixture was prepared by reacting 250 g of DOW CORNING® Q2-8175 Fluid with 11.36 g gluconolactone. The reaction was performed in ethanol solvent at 74° C. until the amine value in the polymer reached to 0.25±0.05. In the second step, 3.5 g acetic anhydride was added to 238 g the reaction mixture (~50% concentration). The molar ratio of secondary amine to AA was 1.0:1.0. The reaction was continued at 75° C. for 5.5 hours. H-NMR was used to confirm the completion of reaction. Ethanol solvent was then stripped under vacuum. The resulting copolymer was characterized by NMR, and dynamic viscosity was checked on ARES Rheometer.

Example-4b

Secondary Amine of Aminoethylaminoisobutyl Reacted with AA

A trimethylsiloxy-terminated, secondary amine functional polydimethylsiloxane having a DP of 350 and which contained 2 pendant aminoethylaminoisobutyl functionalities (300 g) was reacted with gluconolactone (4.14 g) in 200 g ethanol solvent at 74° C. for 6 hours to form a reaction mixture. The amine content in the polyorganosiloxane after the reaction reduced from 0.155 to 0.074 meq/g. H-NMR confirmed the consumption of primary amines by gluconolactone through amide linkage. In the second step, 1.12 g acetic anhydride (AA) was added to 242 g of the reaction mixture (60.3% concentration) and reacted at 74 C for 9 hours. The secondary amine of polyorganosiloxane reacted with AA and formed acetic acid as a byproduct. Ethanol solvent and acetic acid were stripped at 1 mm/Hg vacuum. The resulting copolymer was characterized by NMR.

Example-5a

Secondary Amine of Aminoethylaminopropyl Reacted with DCL

A trimethylsiloxy-terminated, secondary amine functional polydimethylsiloxane having a DP of 350 and containing 2 terminal aminoethylaminopropyl functionalities (400 g) was reacted with gluconolactone (4.96 g) in 100 g ethanol solvent at 74° C. for 7 hours. The amine content in the polyorganosiloxane after the reaction reduced from 0.138 to 0.078 meq/g. H-NMR confirmed the consumption of primary amines of the polyorganosiloxane by gluconolactone through amide linkage. In the second step, 1.80 g 1-chlorodecane (DCL) was added to 170.5 g of reaction mixture (61.8% concentration) and reacted at 74° C. for 9 hours. The secondary amine of the polyorganosiloxane was difficult to react with decyl chloride, and the reaction did not go to completion (20% reacted). Ethanol solvent was stripped under vacuum. The resulting polymer was characterized by NMR.

Example-6a

Epoxysiloxane Reaction with N-Methylglucamine

A polydimethylhydrogensiloxane with a DP of 100 and containing 2 terminal hydrogen bonded silicon atoms (200 g) was reacted with 4.95 g allylglycidylether (AGE) in the presence of 0.10 g Pt IV/IPA catalyst solution (5 ppm Pt). The hydrosilylation reaction to form an epoxy functional polyorganosiloxane was complete in 3 hours at 100 to 120° C. as shown by no SiH peak was observed in FTIR spectra. The epoxy functional polyorganosiloxane (100 g) was then reacted with 4.2 g N-methylglucamine in 100 g ethanol solvent at 75° C. The reaction was complete in ~11 hours. Ethanol solvent was stripped under vacuum. The resulting copolymer was characterized by NMR.

Example-6b

Epoxysiloxane Reaction with N-Methylglucamine

A polydimethylhydrogensiloxane containing 2 terminal hydrogen bonded silicon atoms (200 g) was reacted with 1.60 g allylglycidylether (AGE) in 108 g toluene in the presence of 0.10 g Pt IV/IPA catalyst solution (5 ppm Pt). The hydrosilylation reaction to form an epoxy functional polyorganosiloxane was complete in 5.5 hours at 85 to 95° C. as shown by no SiH peak was observed in FTIR spectra. The epoxy functional polyorganosiloxane (201.5 g) was then reacted with 2.7 g N-methylglucamine in 201.5 g of a solvent mixture of ethanol IPA (1:1 by weight) at 74° C. The reaction was complete in ~11 hours. Ethanol and IPA solvents were stripped under vacuum. The resulting copolymer was characterized by NMR.

Example-6c

Epoxysiloxane Reaction with N-Methylglucamine

A trimethylsiloxy-terminated polydimethylhydrogensiloxane containing 1.87 pendant SiH groups (200 g) was reacted with 1.94 g allylglycidylether (AGE) in the presence of 0.12 g Pt IV/IPA catalyst solution (5 ppm Pt). The hydrosilylation reaction to form an epoxy functional polyorganosiloxane was complete in 3.5 hours at 90 to 100° C. as shown by no SiH peak was observed in FTIR spectra. The epoxy functional polyorganosiloxane (160 g) was then reacted with 2.68 g N-methylglucamine in 160 g ethanol IPA (1:1 by weight) solvent at 74° C. The reaction was complete in 8 hours. Ethanol and IPA solvents were stripped under vacuum. The resulting copolymer was characterized by NMR.

Example-6d

Epoxysiloxane Reaction with N-Methylglucamine

A trimethylsiloxy-terminated polydimethylhydrogensiloxane containing 4 pendant SiH groups (160 g) was reacted with 1.94 g AGE in 100 g toluene in the presence of 0.12 g Pt IV/IPA catalyst solution (5 ppm Pt). The hydrosilylation reaction was complete in 4.5 hours at 85 to 100° C. as shown by no SiH peak was observed in FTIR spectra. The resulting epoxy functional polyorganosiloxane (140 g) was then reacted with 2.9 g N-methylglucamine in 220 g ethanol IPA (1:1 by weight) solvent at 74° C. The reaction was complete in ~9 hours. Ethanol and IPA solvents were stripped under vacuum. The resulting copolymer was characterized by NMR.

Example-7

Aminopropyl Functional Siloxane Based Saccharide Siloxane Copolymers

Aminopropyl functional polyorganosiloxanes have only primary amines in the molecule and, therefore, the reaction with gluconolactone leaves no unreacted amines for protection. These copolymers were hydrolytically stable when emulsified and heat aged at 50° C. The following examples illustrate the synthesis of aminopropyl functional siloxanes.

Example-7a

Aminopropyl Functional Siloxane Based Saccharide Siloxane Copolymers

A trimethylsiloxy-terminated, amine functional polydimethylsiloxane having DP of 350 and containing 2 pendant aminopropyl functionalities (300 g) was reacted with 4.06 g gluconolactone in 203 g ethanol solvent at 74° C. for 8.5 hours. The amine content in the polyorganosiloxane after the reaction was 0.003 meq/g. H-NMR confirmed the consumption of all primary amines of the amine functional polyorganosiloxane by gluconolactone through amide linkage. Ethanol solvent was then stripped under vacuum. The resulting copolymer was characterized by NMR.

Example-7b

Aminopropyl Functional Siloxane Based Saccharide Siloxane Copolymers

A trimethylsiloxy-terminated, amine functional polydimethylsiloxane having DP of 350 and containing 4 pendant aminopropyl functionalities (250 g) was reacted with 6.72 g gluconolactone in 250 g ethanol solvent at 74° C. for 10 hours. The amine content in the polyorganosiloxane after the reaction reduced from 0.151 to 0.014 meq/g. H-NMR confirmed the consumption of all primary amines of the polyorganosiloxane by gluconolactone through amide linkage. Ethanol solvent was then stripped under vacuum. The copolymer was characterized by NMR.

Example 8

A polydiorganosiloxane having aminoethylaminopropyl functional groups was prepared by mixing 987.87 g of linear silanol functional polydimethylsiloxane fluid, and 15.56 g (76.1 mmole) of methylaminoethylaminoproyldimethylethoxysilane. To this mixture was added 4.0 g (27.7 mmole) of octanoic acid. This mixture was heated with stirring for 4 h at 95°±5° C. The mixture was then stripped of volatiles by heating to 120°±5° C./25 mmHg and maintaining these conditions for 3 hours. Characterization by 1H, 13C and 29Si NMR indicated that the desired reaction had occurred.

To a mixture of 303.74 g of a polydiorganosiloxane made from reaction of the telechelic aminoethylaminopropyl functional polydimethylsiloxane and gluconolactone (0.07 meg amine/g polymer) and 200 g ethanol was added 1.8 g (0.024 mole) of glycidol. This mixture was heated with stirring for 4 h at 75°±5° C. At this point, the H-NMR indicated that the reaction had completed. Most of the ethanol was removed on a rotary evaporator by heating to 50°±5° C. and <35 mmHg. The crude product was placed on a high vacuum line overnight to remove the remainder of the ethanol. Characterization by 1H, 13C and 29Si NMR and amine titration indicated that the desired reaction had occurred to form a copolymer.

Example 9

A polymer was prepared as in example 1a by reacting DOW CORNING® Q2-8175 Fluid (Dow Corning Corp., Midland, Mich.), a 150-400 cst. trimethylsiloxy-terminated, polydimethylsiloxane with pendant aminoethylaminoisobutyl groups (approximately 2.3 mole percent), with gluconolactone.

To a mixture of 120.76 g of the polymer (0.250 meg amine/g polymer) in 79.24 g ethanol was added 2.24 g (30.0 mmole) glycidol. This mixture was heated with stirring for 4 h at 75°±5° C. At this point, the 1H-NMR indicated that the reaction had completed. Most of the ethanol was removed on a rotary evaporator by heating to 50°±5° C. and <35 mmHg. The crude product was placed on a high vacuum line overnight to remove the remainder of the ethanol. Characterization by 1H, 13C and 29Si NMR and amine titration indicated that the desired reaction had occurred to form a copolymer.

Example 10

To a mixture of 981.7 g of linear silanol functional polydimethylsiloxane fluid was added 11.1 g (68.8 mmoles) of hexamethyldisilazane and 0.05 g of trifluoroacetic acid. The mixture was heated and maintained at 60°±5° C. for 1.5 h. Next, 8.37 g (38.1 mmoles) of aminoethylaminoisobutylmethyldimethoxysilane was added with 2.0 g of octanoic acid. This mixture was heated with stirring for 4 h at 95°±5° C. The mixture was then stripped of volatiles by heating to 120°±5° C./25 mmHg and maintaining these conditions for 3 hours. Characterization by 1H, 13C and 29Si NMR indicated that the desired reaction had occurred to form a polyorganosiloxane having 2 pendant aminoethylaminoisobutyl groups.

To a mixture of 100.01 g of the polyorganosiloxane (prepared above) having 2 pendant aminoethylaminoisobutyl groups (0.145 meg amine/g polymer) and 200.10 g ethanol was added 1.29 g (7.0 mmole) of gluconolactone. The mixture was heated with stirring for 4 h at 75°±5° C. Amine titration indicated that half of the amine had been reacted. Next, 0.54 g (7.3 mmole) of glycidol was added and the mixture was heated with stirring for 4 h at 75 °±5° C. At this point, the 1H-NMR indicated that the reaction had completed. Most of the ethanol was removed on a rotary evaporator by heating to 50°±5° C. and <35 mmHg. The crude product was placed on a high vacuum line overnight to remove the remainder of the ethanol. Characterization by 1H, 13C and 29Si NMR and amine titration indicated that the desired reaction had occurred to form a copolymer.

Example 11

A polydiorganosiloxane having aminoethylaminopropyl functional groups was prepared by mixing 987.87 g of linear silanol functional polydimethylsiloxane fluid, and 15.56 g (76.1 mmole) of methylaminoethylaminoproyldimethylethoxysilane. To this mixture was added 4.0 g (27.7 mmole) of octanoic acid. This mixture was heated with stirring for 4 h at 95°±5° C. The mixture was then stripped of volatiles by heating to 120°±5° C./25 mmHg and maintaining these conditions for 3 hours. Characterization by 1H, 13C and 29Si NMR indicated that the desired reaction had occurred to form a telechelic aminoethylaminopropyl functional polyorganosiloxane.

To a mixture of 150 g of the telechelic aminoethylaminopropyl functional polyorganosiloxane prepared above (0.14 meq amine/g polymer) and 150 g ethanol was added 2.23 g (30.1 mmole) of glycidol. This mixture was heated with stirring for 4 h at 75 °±5° C. At this point, the 1H-NMR indicated that the reaction had completed. Most of the ethanol was removed on a rotary evaporator by heating to 50°±5° C. and <35 mmHg. The crude product was placed on a high vacuum line overnight to remove the remainder of the ethanol. Characterization by 1H, 13C and 29Si NMR and amine titration indicated that the desired reaction had occurred to form a copolymer.

Example-12

Aminopropyl Functional Siloxane Based Saccharide Siloxane Copolymers

A saccharide siloxane having DP of 350 with terminal saccharide components was prepared by reacting a polyorganosiloxane having terminal aminoethylaminopropyl groups with gluconolactone in the first step. Ethanol solvent was used to facilitate the reaction. Once all the primary amines were converted to amides by reacting with gluconolactone, capping agents (e.g., AGE, DGE or AA) were reacted with remaining secondary amines in the second step.

Example-12a

Comparative

A polyorganosiloxane having two terminal aminoethylaminopropyl groups and a DP of 350 (300 g) containing 0.140 meq amine/g was reacted with gluconolactone (3.74 g). Amine content in the polyorganosiloxane reduced to 0.067 meq/g. Ethanol was stripped from the reaction mixture under vacuum and a viscous product was obtained. H-NMR confirmed the complete reaction of primary amines with gluconolactone. The product was heat aged at 50° C. for 3 weeks and characterized by H-NMR and viscosity measurement using an ARES Rheometer. Results are in Table 1.

Example-12b

The reaction mixture from example 12a containing 0.040 meq amine/g (229 g) was reacted with allylglycidylether at 74° C. for 8 hours. H-NMR showed complete reaction of secondary amine with epoxy groups of AGE. Ethanol solvent was then stripped under vacuum and a viscous copolymer was obtained. The copolymer was heat aged at 50° C. for 3 weeks and characterized. The copolymer viscosity was checked on the ARES Rheometer. Results are in Table 1.

Example-12c

The reaction mixture from the example 12a containing 0.040 meq amine/g (262 g) was reacted with dodecylglycidylether at 74° C. for 8 hours. H-NMR showed complete reaction of secondary amine with epoxy groups of DGE. Ethanol solvent was then stripped under vacuum and a viscous copolymer was obtained. The copolymer was heat aged at 50° C. for 3 weeks and characterized. The copolymer viscosity was checked on the ARES Rheometer. Results are in Table 1, below.

Example-12d

A reaction mixture was prepared as in example 12a. The reaction mixture contained 0.045 meq amine/g, and this reaction mixture (240 g) was reacted with acetic anhydride at 74° C. for 8 hours. H-NMR showed complete reaction of the secondary amine with anhydride functionality. Ethanol solvent was then stripped under vacuum and a viscous copolymer was obtained. The copolymer was heat aged at 50° C. for 3 weeks and characterized. The copolymer viscosity was checked on a Rheometer.

Example 13

To a mixture of 150 g of a polyorganosiloxane (having a DP of 350 and terminal SiH groups) and 150 g of 2-propanol (IPA), was added 0.3 g of sodium acetate and 2.13 g (11.5 mmole) of allyl xylitol. The mixture was heated with stirring to 60°±5° C. when 0.454 g of a 1 weight percent solution of chloroplatinic acid (CPA) in IPA (7 ppm Pt) was added. The mixture was then heated with stirring for 7 h at 75°±5° C. Analysis of the reaction by FTIR indicated that >95% of the SiH had been consumed. Most of the IPA was removed on a rotary evaporator by heating to 60°±5° C. and <35 mmHg. The crude product was placed on a high vacuum line overnight to remove the remainder of the IPA. Characterization by 1H, 13C and 29Si NMR indicated that the desired reaction had occurred to form a copolymer.

Example 14

Polymer Emulsification, Speed Mixer

A copolymer (47.5 grams) from the examples above was blended with Isofol 12 (2-butyloctanol) from Sasol Co. (2.5 grams), and further blended with Tergitol 15-s-3 (which is a secondary ethoxylated (~3) alcohol with 11 to 15 carbon atoms) from the Dow Chemical Company of Midland, Mich., USA (1.0 grams) via a Hauschild Engineering Speed Mixer (Model # DAC 150 FZ) with a speed of 3500 rpm for 15 seconds in a max 100 cup. Tergitol 15-s-40 (a secondary ethoxylated (~40) alcohol with 11 to 15 carbon atoms, 70% active in water) also from Dow Chemical Company (5.5 grams) and de-ionized water (4.5 grams) were added and immediately subjected to high levels of mixing shear as provided by the Speed Mixer. Typically, 4 cycles of mixing at 3500 rpm for 25 seconds each followed by mixer cup scraping were needed to fully transition the mixture to an oil-in-water configured emulsion. Subsequent incremental additions of de-ionized water (totaling 39.0 grams) were also completed using the Speed Mixer. Post additions of preservatives into the water phase were made, consisting of Phenoxetol-Low Phenol (Phenoxyethanol) from Clariant (0.9 grams) and Neolone 950 (methylisothiazolinone, 9.5% in water) from Rohm and Haas (0.079 grams). All mixing was completed at atmospheric pressure and at room temperature with some heat being generated during the inversion step to approximately 40° C. The resulting product was an oil in water emulsion with a mono-modal particle size distribution having a volume average particle diameter of 300.0 nanometers as measured by a Malvern particle size analyzer (model # MS-S). The copolymers were tested and the results are in Table 1. The product had a Non-Volatile Content (NVC) of 55% when two grams of emulsion was subjected to two hours at 105° C.

Example 15

Polymer Emulsification, Change Can Mixer

One of several variations of a saccharide siloxane copolymer (2042.5 grams) prepared in the above examples was blended with Isofol 12 (2-butyloctanol) from Sasol Co. (107.5 grams) and was further blended with Tergitol 15-s-3 (C11-C15 secondary ethoxylated (~3) alcohol) from Dow Chemical Company (42.8 grams) via a Ross change can mixer equipped with 2 disperser blades and an anchor style scraper blade commonly called a tri-shaft design (Model # VMC-1) with a speed of 40 rpm on the scraper blade for 3 minutes. Tergitol 15-s-40 (C11-C15 secondary ethoxylated (~40) alcohol, 70% active in water) from Dow Chemical Company (236.8 grams) and de-ionized water (100.9 grams) were added and immediately subjected to high levels of mixing shear as provided by the Ross Mixer. Typically 2 cycles of mixing at 4000 rpm on the disperser blades and 40 rpm on the scraper blade for 3 minutes each followed by mixer scraping with a spatula of both the blades and pot were needed to fully transition the mixture to an oil-in-water configured emulsion. Subsequent incremental additions of de-ionized water (totaling 1727 grams) were also completed using the Ross Mixer. Post additions of preservatives were made into the water phase, consisting of Phenoxetol—Low Phenol (Phenoxyethanol) from Clariant (38.7 grams) and Neolone 950 (methylisothiazolinone, 9.5% in water) from Rohm and Haas (3.4 grams). All mixing was completed under vacuum at a level of 20 in Hg to minimize foaming. Natural heat was generated during the inversion step and cooling was utilized on the mixer pot jacket to maintain temperature below 40° C. The resulting product was an oil in water emulsion with a monomodal particle size distribution having a volume average particle diameter of 300.0 nanometers as measured by a Malvern particle size analyzer (model # MS-S) and with a Non-Volatile Content (NVC) of approximately 55% when two grams of emulsion was subjected to two hours at 105° C.

Example 16

Internal Phase Extraction

The internal phase of the oil-in-water emulsion prepared in example 14 was extracted by adding 10 grams of emulsion to a centrifuge tube followed by the addition of 30-40 grams of acetone. The mixture was blended by hand or other method to disperse the acetone. The tubes were placed into a centrifuge with a G-force of 3600 (5 cm @ 8000 rpm, accuspin model #400). The non-polymer layer which was usually on the top was decanted from the tube. The acetone/water/surfactant/Isofol/preservative mixture was collected into a separate container for further analysis. Two or three cycles of acetone, mixing, and centrifugation were required to remove all but small traces of the water, surfactants, Isofol and preservatives from the emulsion which were evident visually with the appearance of a clear polymer layer. This clear polymer layer was then poured into a suitable aluminum drying pan and placed into a chemical fume hood for overnight drying. The extraction procedure was completed within a few days of producing the emulsion as well as after the emulsion was stored for some time at either room temperature or 50° C. (typically 7 days at 50° C.).

Example 17

Internal Phase Rheological Measurement

Dried emulsion extracts containing mainly copolymer were examined for dynamic viscosity using a Rheometric Scientific rheometer (model # ARES) utilizing 40 mm parallel plates with a gap of 1 mm. A dynamic frequency sweep was conducted at 10% strain ranging from 0.05 Hz to 80 Hz. Analysis was conducted by plotting the original scan compared with heat and room temperature aged extractions. Results are in Table 1, below, for the samples tested.

Example 18

NMR Characterization

For each copolymer tested, 0.2 g of sample was weighed into a small vial, and 0.175 g of CD3OD (Aldrich) and 2.5-2.7 g of CDCl3 containing 0.03% toluene were added to the vial containing the sample and mixed until miscible. Proton NMR spectra were generated using a Varian Mercury 300 MHZ spectrometer. Functional group concentrations were obtained by peak integration of both the characteristic sample peaks and the toluene internal standard. The aldonamide proton on the carbon adjacent to the carbonyl was used to determine the aldonamide concentration by using an internal standard. The aldonamide concentration was compared after aging for 4 weeks at 50° C. to the initial concentration to determine the change in concentration. The results are in Table 1.

Example 19

Wet Combing Test

Samples of certain copolymers described above were formulated into hair conditioning compositions. The wet combing test was used to screen the conditioning benefit of the copolymers. When using a tensile tester, the friction force while moving a comb through wet hair tress was measured to indicate ease of comb. The combing force reduction correlated to the conditioning of the hair. The tensile tester used was Instron model 4644, each hair tress was of comparable defined weight, width, length and type; combs were with defined spacing and material. Hair tresses were washed and rinsed with the compositions at controlled temperatures. Combing force measurements were carried out in a climate controlled room of constant temperature and humidity. Results of the wet combing test on the hair samples are in Table 1, below.

TABLE 1

| Example | Example 19 Wet combing 6-8 wk 50° C. | Example 17 Rheology trendline @ 4 wks 50° C. % retention (extracted emulsion) | Example 18 H NMR Aged 4 wks 50° C. % retention (extracted emulsion) | Example 17 Initial internal phase viscosity (Pas) | Malvern S Particle Size D(v, 0.5) (μm) |
|---|---|---|---|---|---|
| 2a | 0.032 | 20 | 55 | 137 | 0.261 |
| 9 | 0.033 | 68 | 30 | | 0.36 |
| 3a | 0.041 | 35 | 48 | 1523 | 0.337 |
| 8, 11 | 0.041 | 17 | 30 | | 0.433 |
| 6a | 0.041 | 51 | 38 | 216 | 0.2 |
| 6c | 0.043 | 60 | 77 | 44 | 0.485 |
| 12c | 0.057 | 4 | 32 | 120 | 0.38 |
| 6d | 0.059 | 32 | 60 | 450 | 0.696 |
| 2b | 0.196 | 12 | 33 | 76 | 0.347 |

TABLE 1-continued

| Example | Example 19 Wet combing 6-8 wk 50° C. | Example 17 Rheology trendline @ 4 wks 50° C. % retention (extracted emulsion) | Example 18 H NMR Aged 4 wks 50° C. % retention (extracted emulsion) | Example 17 Initial internal phase viscosity (Pas) | Malvern S Particle Size D(v, 0.5) (μm) |
|---|---|---|---|---|---|
| 12b | 0.196 | 3 | 30 | 195 | 0.353 |
| 4b | 0.484 | 25 | 59 | 136 | 0.397 |
| 12a Comparative | 0.532 | 0.5 | 8 | 310 | 0.343 |
| 7a | 0.653 | 80 | 79 | 44 | 0.361 |
| 1b | 0.150 | | | 97 | 0.318 |
| 1e Comparative | 0.208 | | | 595 | 0.268 |

The invention claimed is:

1. A saccharide siloxane copolymer of formula:

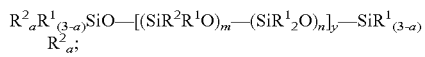

$R^2_a R^1_{(3-a)} SiO-[(SiR^2R^1O)_m-(SiR^1_2O)_n]_y-SiR^1_{(3-a)} R^2_a$;

where each $R^1$ can be the same or different and each $R^1$ comprises hydrogen, an alkyl group, an organic group, or a group of formula $R^3$-Q;

Q comprises an epoxy, cycloalkylepoxy, primary or secondary amino, ethylenediamine, carboxy, halogen, vinyl, allyl, anhydride, or mercapto functionality;

subscripts m and n are integers from 0 to 10,000 and may be the same or different;

each subscript a is independently 0, 1, 2, or 3;

subscript y is an integer such that the copolymer has a molecular weight less than 1 million;

each $R^2$ has formula $Z$-$(G^1)_b$-$(G^2)_c$, and there is an average of at least one $R^2$ per copolymer molecule, where $G^1$ is a saccharide component comprising 5 to 12 carbon atoms, a quantity (b+c) has a value ranging from 1 to 10, and subscript b or subscript c can be 0, $G^2$ is a saccharide component comprising 5 to 12 carbon atoms additionally substituted with organic or organosilicon radicals, each Z is a linking group and is independently selected from the group consisting of: —$R^3$—N($R^8$)—C(O)—$R^4$—, —$R^3$—CH(OH)—CH$_2$-N($R^8$)—$R^4$—, or —$R^3$—CH(N($R^4$)($R^8$))CH$_2$OH;

where each $R^3$ and each $R^4$ are divalent spacer groups comprising a group of formula $(R^5)_r(R^6)_s(R^7)_t$, where at least one of subscripts r, s and t is 1, and each $R^5$ and each $R^7$ are independently either an alkylene group of 1 to 12 carbon atoms or a group of formula $(R^9O)_p$, where subscript p is an integer with a value ranging from 1 to 50, and each $R^9$ is a divalent organic group, and each $R^9$O may be the same or different, each $R^6$ is —N($R^8$)—, where $R^8$ is selected from $R^3$, a group of formula Z—X, an unsaturated hydrocarbon group, or a reaction product of —N(H)— with an epoxy functional group, a cycloalkylepoxy functional group, a glycidyl ether functional group, an acid anhydride functional group, or a lactone;

each X is independently a divalent carboxylic acid, phosphate, sulfate, sulfonate or quaternary ammonium radical, and with the provisos that at least one of $R^3$ and $R^4$ must be present in the linking group, and each $R^3$ and each $R^4$ may be the same or different.

2. The copolymer of claim 1, where subscript y is greater than 0 and at least one of subscript m and subscript n is greater than 0.

3. The copolymer of claim 1 where each subscript a is 0 and each $R^1$ is an alkyl group of 1 to 12 carbon atoms.

4. A method for making a copolymer of claim 1 comprising:
1) reacting an amine functional polyorganosiloxane, containing a primary amine and a secondary amine, with a sugar lactone,
2) reacting the product of step 1) with a capping agent selected from a lactone, a halogenated unsaturated compound, an epoxy functional compound, or an acid anhydride.

5. The method of claim 4, where the sugar lactone is an aldonolactone.

6. The method of claim 4, where the lactone in step 2) is selected from: butyrolactone, epsilon caprolactone, gamma gluconolactone, delta gluconolactone, and lactobionolactone.

7. The method according to claim 4, where the halogenated unsaturated compound is an alkenyl chloride.

8. The method according to claim 4, where the epoxy functional compound is selected from allyl epoxy functional compounds, cycloalkylepoxy functional compounds, glycidyl ether functional compounds, and glycidol.

9. The method according to claim 4, where the acid anhydride comprises acetic anhydride, chloroacetic anhydride, propionic anhydride, crotonic anhydride, methacrylic anhydride, butyric anhydride, isobutyric anhydride, diethyl pyrocarbonate, or 4-pentenoic anhydride.

10. A method for making a copolymer according to claim 1 comprising: 1) reacting an epoxy functional polyorganosiloxane with an n-alkyl glucamine.

11. The method of claim 10, where the ingredients further comprise an alkene.

12. A method for making a copolymer according to claim 1 comprising: 1) reacting an n-alkyl-glucamine with an alkenyl functional epoxy compound, and 2) hydrosilylating the product of step 1) with a polyorganohydrogensiloxane.

13. The method of claim 12, where the n-alkyl glucamine is n-methyl glucamine.

14. A composition comprising:
(A) the copolymer according to claim 1 and
(B) an additional ingredient.

15. The composition of claim 14, where ingredient (B) comprises:
(ii) a carrier medium suitable to permit topical application composition to a portion of the body,
(iii) a cross-linker,
(iv) a surfactant, or
(v) a combination thereof.

16. The composition of claim 15, where ingredient (iii) is present, and ingredient (iii) comprises water.

17. The composition of claim 16, where the composition is an emulsion.

18. The composition according to claim 14 where the composition is a personal care composition adapted to provide a benefit to a portion of the body to which it is applied.

* * * * *